(12) United States Patent
Robson (10) Patent No.: US 10,660,516 B2
(45) Date of Patent: May 26, 2020

(54) SYSTEM AND METHOD FOR MEASUREMENT OF CONTRAST SENSITIVITY

(71) Applicant: PRECISION VISION, INC., Woodstock, IL (US)

(72) Inventor: John Robson, Cambridge (GB)

(73) Assignee: PRECISION VISION, INC., Woodstock, IL (US)

(*) Notice: Subject to any disclaimer, the term of this patent is extended or adjusted under 35 U.S.C. 154(b) by 89 days.

(21) Appl. No.: 15/925,254

(22) Filed: Mar. 19, 2018

(65) Prior Publication Data

US 2018/0263487 A1   Sep. 20, 2018

Related U.S. Application Data

(60) Provisional application No. 62/473,416, filed on Mar. 19, 2017.

(51) Int. Cl.
*A61B 3/02* (2006.01)
*A61B 3/032* (2006.01)
*A61B 3/06* (2006.01)

(52) U.S. Cl.
CPC .............. *A61B 3/022* (2013.01); *A61B 3/032* (2013.01); *A61B 3/063* (2013.01)

(58) Field of Classification Search
CPC .......... A61B 3/022; A61B 3/063; A61B 3/032
USPC ........................................ 351/200, 222, 239
See application file for complete search history.

(56) References Cited

U.S. PATENT DOCUMENTS

2017/0273553 A1*   9/2017   Greivenkamp, Jr. ... A61B 3/032

* cited by examiner

*Primary Examiner* — Tuyen Tra
(74) *Attorney, Agent, or Firm* — Pauley Erickson & Kottis (57) ABSTRACT

An apparatus and method for evaluating a patient's contrast sensitivity. The apparatus including a table or chart with a plurality of shaded marks printed in cells in the table or chart. The shaded marks printed with a various contrasts with a log of Weber contrast ranging from −0.20 to −2.15. Where a subject marks an observed position of the shaded marks and a key is used to check the observed position against an actual position of the shaded mark to determine a threshold contrast of the subject.

20 Claims, 8 Drawing Sheets

SYSTEM AND METHOD FOR MEASUREMENT OF CONTRAST SENSITIVITY

This application claims the benefit of U.S. Provisional Application, Ser. No. 62/473,416, filed on 19 Mar. 2017. The co-pending parent application is hereby incorporated by reference herein in its entirety and is made a part hereof, including but not limited to those portions which specifically appear hereinafter.

BACKGROUND OF THE INVENTION

Field of the Invention

The invention relates to a system and method for measurement of a patient's contrast sensitivity. The system and method of this invention is particularly useful for differentiating diabetic patients with different levels of retinopathy. The system and method is also useful for detection or evaluation of other ocular diseases including, but not limited to, age-related macular degeneration, glaucoma, and multiple sclerosis.

Description of Prior Art

Approximately 250 years ago, Pierre Bouguer reported that a shadow of a vertical rod cast by a distant candle on a white screen illuminated by another nearer candle could be seen so long as the distant candle was no more than eight times as far from the screen as the nearer candle. Based on this observation, Bouguer calculated that a diminution in the illumination of one area of an image with respect to an adjacent area of 1 part in 64 could be detected with normal human vision. The measurement that Bouguer had made of what would now be called "threshold contrast" constituted the earliest quantitative measurement of visual function. In the mid-$19^{th}$ century, Masson, a physicist, developing new methods of photometry, noted that there was some individual variation in visual contrast threshold, and was the first to suggest that this might be of physiological and medical interest. Even then, it was not until the end of the $19^{th}$ century that it was more widely recognized that contrast threshold could be raised (i.e. contrast sensitivity reduced) in various ocular conditions in which visual acuity might be no more than slightly compromised and the potential clinical usefulness of contrast sensitivity measurements began to be appreciated and noted in the text books of that period. Despite this appreciation, the clinical measurement of contrast sensitivity has to this day remained little more than a curiosity although various methods of measurement have been developed and described since that time.

There are two main reasons why the measurement of contrast sensitivity has not been more widely adopted in clinical opthalmological and optometric practice. Firstly, the major application of visual function measurement has been in optimizing the optical correction of refractive error and the adequacy of measurement of visual acuity, coupled with the simplicity of chart-based methods of determining it, has made this the measure of visual function with which everyone is familiar and the one which has become the sine qua non of opthalmological and optometric examination. In the context of refractive correction a measurement of contrast sensitivity is relevant only if acuity cannot be brought up to normal levels optically and even then may not be particularly useful except as confirmation of the existence of some underlying ocular disorder. It is rarely helpful in differential diagnosis. Moreover, to the extent that it is necessary to characterize the severity of the visual impairment that results from such disorders, the reduction in acuity compared with that of subjects with normal vision has been generally accepted as an adequate measure. Secondly, there has not, until relatively recently, been any way to measure a patient's contrast sensitivity that has been sufficiently acceptable to clinicians to encourage the adoption of this measure of visual function in routine clinical practice. This is somewhat surprising since the desirability of having a method of measuring contrast sensitivity that was as simple and reliable as that for determining visual acuity was appreciated by Bull (1882) within twenty years of the first publication of the standardized letter charts (Snellen, 1862) that had originally prompted the widespread use of such charts for clinical measurement of visual acuity. Bull proposed that contrast sensitivity should be measured using a chart with letters all of the same large size whose contrast with respect to their white background decreased progressively from the top to the bottom of the chart, the letters being black at the top of the chart and then becoming fainter and fainter on successive lines until those at the bottom were invisible. This chart would be used in much the same way as an acuity chart, the contrast threshold being recorded as the contrast of the faintest letters that could be correctly named. It was a good idea but, unfortunately, Bull was unable to make such a chart.

Figure 1:
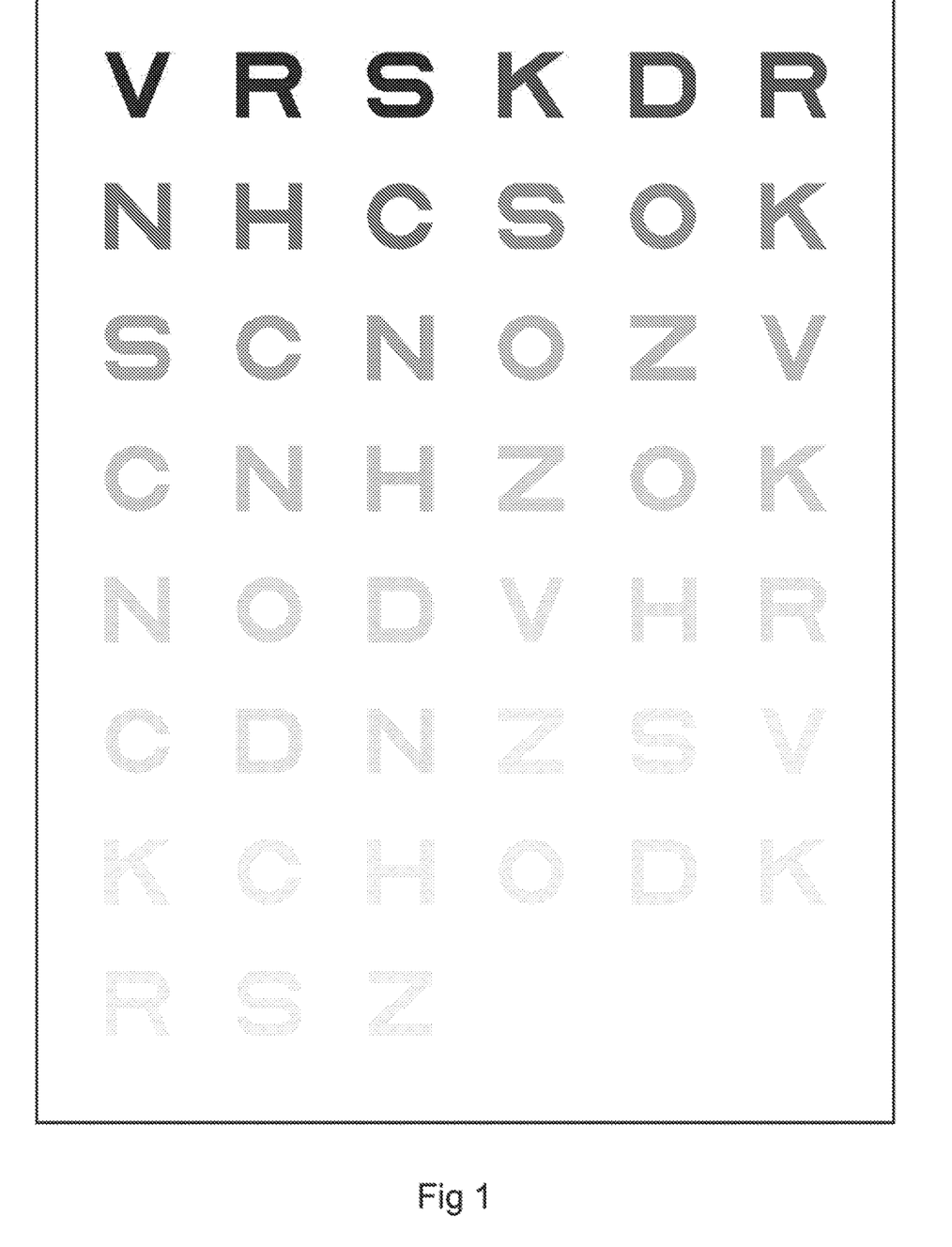
FIG. 1 is a prior art example of a contrast sensitivity chart.

In 1988, Pelli, Robson and Wilkins designed and manufactured such a letter contrast sensitivity chart, see FIG. 1, using the latest technical advances in printing methods. These letter charts provided a more practicable way of measuring contrast sensitivity in the clinic than laboratory-style systems based on electronic display devices and have undoubtedly increased interest in the clinical application of contrast sensitivity measurement, particularly in the assessment of low vision. However, it is still seems that although numerous studies have shown that reduction in contrast sensitivity can provide a useful measure of disease progression, such measurements are not routinely made to aid the management and treatment of progressive diseases in opthalmological practice. The reason for this is perhaps to be sought in the fact that clinicians working in a clinic will normally assess a patient's disease status using funduscopic and tomographic methods and would gain little from any measurement of visual function.

However, there are other circumstances in which it may be more appropriate to consider making measurements of visual function as an aid to management of disease such as, but not limited to, age-related macular degeneration (AMD) and diabetes. One known chart is the Amsler grid that is used for monitoring the progression of AMD and to provide information related to other diseases, such as diabetes.

SUMMARY OF THE INVENTION

The present invention provides a device and method for measuring contrast sensitivity of patients with ocular disease. This invention is particularly useful for evaluating diabetic patients and patients with age-related macular degeneration, whose contrast sensitivity is known to be progressively reduced by these diseases. Multiple sclerosis is another disease where contrast sensitivity is used to measure the onset and progression of the disease.

In an embodiment of the invention, the apparatus comprises a table or chart with a plurality of cells arranged in rows and columns. In one embodiment, the table includes twenty-five rows and four columns of elongated rectangles. However, the invention is not limited to twenty-five rows and four columns of elongated rectangles and may comprise any number and arrangement of cells. In another embodiment, the chart may comprise a plurality of lattices, each of the lattices including a plurality of cells. For example, each lattice may comprise a large square divided into a plurality of smaller squares, such as nine squares divided in a 3×3 arrangement. However, it should be understood that the chart is not limited to the described chart and may comprise other arrangements.

In accordance with this invention, a shaded mark is positioned in each of the elongated rectangles. Preferably, the shaded mark is located in one of a plurality of positions within each of the elongated rectangles. In one embodiment, the shaded mark is positioned in one of six locations along the elongated rectangle. However, the location is not limited to six positions and may comprise any plurality of positions. In another embodiment, the shaded marks are located in one or more of the cells in each of the lattices and absent from the remaining cells. For example, a 3×3 lattice may include two squares, each containing one of the shaded marks, and seven empty squares. It should be understood that this invention may include alternative positioning of the shaded marks.

In a preferred embodiment, the shaded mark comprises a circular spot with a diameter of 9 mm. However, the shaded mark is not limited to this shape and diameter and may comprise other shapes and dimensions. In a preferred embodiment, the shade marks maintain the same shape for the entire chart.

In an embodiment of this invention, each of the shaded marks varies in a level of contrast with a log of Weber contrast ranging from −0.05 to −2.30. In a more preferred embodiment, the log of Weber contrast ranges from −0.20 to −2.15. In a most preferred embodiment, the log of Weber contrast ranges from −0.85 to −2.05. In an embodiment of this invention, the plurality of shaded marks in each of the rows maintain a consistent contrast and the shaded marks become increasingly faint from the top of the chart to the bottom of the chart. For example, in an embodiment with twenty-five rows, the top row has a log of Weber contrast of −0.85 and each subsequent row is 0.05 lower until the bottom row has a log of Weber contrast of −2.05. In another embodiment, in a chart with twenty 3×3 lattices arranged in a 4×5 layout, the upper left lattice may include shaded marks with −0.20 and −0.25 log of Weber contrast and moving from left to right and down the page to the lower right lattice with a −2.10 and −2.15 log of Weber contrast. It should be understood that the layout of the shaded marks may vary without departing from teachings of this invention.

In a preferred embodiment, the chart of this invention is printed on paper and preferably a single-use test. By printing the chart on paper the test of this invention is relatively low cost which is particularly helpful to economically disadvantaged areas. Additionally, the single-use nature of the test eliminates issues with long-term maintenance of the contrast of the shaded marks.

In a preferred embodiment of this invention, the system further includes a key for checking an observed position of the shaded mark in comparison to an actual position of the shaded mark. In an embodiment, the key comprises a generally translucent or transparent material with a plurality of indicators identifying locations of the plurality of shaded marks. The generally translucent or transparent material allows the key to be placed on top of the chart to locate the actual positions of the shaded marks.

To use the system of this invention, a patient views the table or chart and marks the center of each of the shaded marks with a writing utensil or another device, starting from an upper left corner moving from left to right and down the page to a lower right hand corner or until the patient can no longer see the shaded marks. The key is then overlaid on the chart and a comparison is made between the observed mark (or believed observed mark) and an actual position of the shaded mark. A faintest shaded mark that is correctly identified is the patient's threshold contrast. A criterion for determining the faintest shaded mark may be determined by the highest row in which the patient correctly identified the position of no more than two of the four shaded marks that is the highest row in which the position of two or more marks was incorrectly recorded. An alternative criterion may be a lattice with the darkest shaded marks in which neither shaded mark was correctly identified. Other alternative criteria may be used, especially if a structure of the chart varies from the embodiments described in this application.

In an alternative embodiment of this invention, scoring of the chart may be accomplished using electronic means, such as photographing or scanning a completed test and a program would look for differences in the test page between marked and unmarked. In another embodiment, the chart of this invention may be provided on a computer with a processor, such as a tablet computer, with a touch sensitive pad and/or a stylus-type marking device.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

This invention provides a system and method for determining contrast sensitivity of a patient or subject.

Figure 2A:
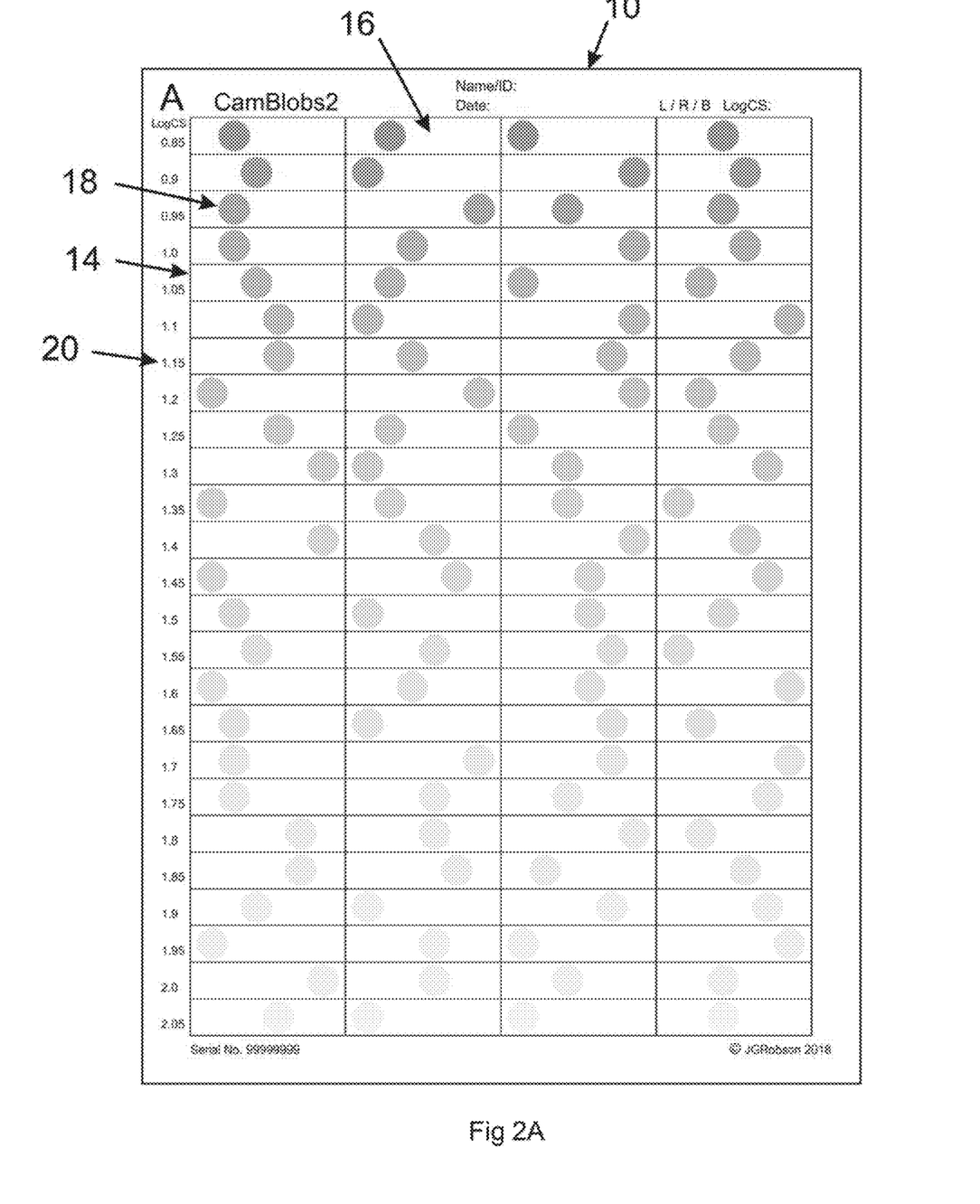
FIG. 2A is a chart for measuring contrast sensitivity according to a preferred embodiment of this invention.
Figure 2B:
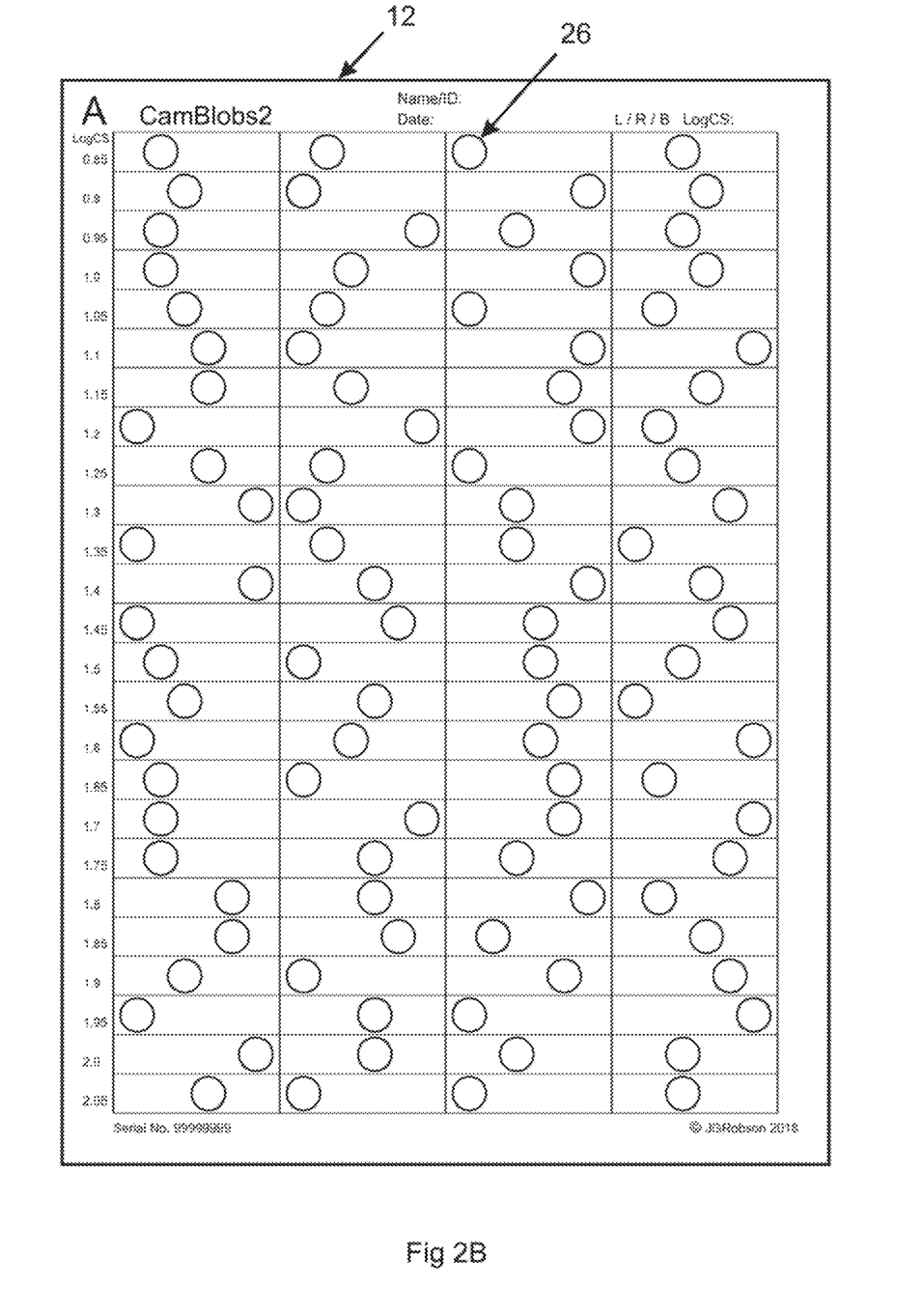
FIG. 2B is a key for the contrast sensitivity chart of FIG. 2A.

FIG. 2A illustrates a chart 10, arranged as a table, for determining contrast sensitivity according to one embodiment of this invention. FIG. 2B illustrates a key 12 for checking the table 10.

In this embodiment, the table 10 comprises a grid 14 having twenty-five rows and four columns of cells 16 defined by thin black lines. In this embodiment, the cells 16 comprise elongated rectangles. However, it should be understood that the table 10 is not limited to this layout and may include an alternative sized grid and cells with a different number of rows and columns or another arrangement, such as a triangular arrangement. The table 10 of FIG. 2A further includes a plurality of shaded marks 18 positioned in each of the elongated rectangles 16 preferably including a single shaded mark 18 in each of the elongated rectangles 16. In this embodiment, the shaded mark 18 comprises a shaded circular spot having a 9 mm diameter. In alternative embodiment, the shaded mark 18 may not comprise a circular spot with a 9 mm diameter and may comprise any shape and/or any dimensions. However, in a preferred embodiment, the plurality of shaded marks 18 comprise a consistent shape throughout the chart 10.

According to this invention, each of the shaded marks 18 has a defined contrast, where contrast is the difference in luminance or color that makes an object (or its representation in an image or display) distinguishable. In a preferred embodiment, the contrast of each of the plurality of shaded marks 18 varies and the contrast sensitivity of the patient is determined by evaluating the patient's ability to distinguish and identify a position of the various shaded marks 18 and the associated varying contrast. There are many possible definitions of contrast, for example Weber contrast, Michelson contrast, and Root mean square (RMS) contrast. In this application, contrast will be measured using a log of Weber contrast. However, it should be understood that other measurement techniques may be used. In an embodiment of this invention, each of the shaded marks 18 varies in a level of contrast with a log of Weber contrast ranging from −0.05 to −2.30. In a more preferred embodiment, the log of Weber contrast ranges from −0.20 to −2.15. In a most preferred embodiment, the log of Weber contrast ranges from −0.85 to −2.05.

In the embodiment shown in FIG. 2A, the shaded marks 18 are printed with a progressively decreasing contrast. At the top of the chart 10, the shaded marks 18 are dark grey relative to the background, while moving down the chart 10 the shaded marks 18 become progressively lighter and lighter relative to the background. In the preferred embodiment shown, the shaded marks 18 located in each row possess a consistent contrast and the contrast decreases for each subsequent row moving down the table 10. Specifically, in the embodiment of FIG. 2A, a top row includes a log Weber contrast of −0.85 (corresponding to a contrast of 14.1%). The Weber contrast of the shaded marks 18 on each successive row is 0.05 log units lower than the row above with a lowest row having a log of Weber contrast of −2.05 (corresponding to a contrast of 0.78%). Charts according to this invention may vary from this standard table design with varying ranges of contrast and with or without consistent contrast on each of the rows. For example, a range of darker contrast ratios may be used to measure contrast sensitivity in patients with more severely impaired vision.

In accordance with this invention, a location of the shaded mark 18 is randomly placed within each of the plurality of elongated rectangles 16. In the embodiment of FIG. 2A, each of the shaded marks 18 randomly occupy one of six equally spaced positions within the elongated rectangle 16. In alternatively embodiments, the shaded marks 18 may be positioned in one of any number of positions. It is the patient's task to identify the position of each spot within each of the elongated rectangles 16 and to indicate the center location by marking a small cross at the center of the shaded mark 18 with a writing utensil or otherwise marking the center. In this embodiment, there are twelve variants of the chart 10 having the shaded marks located in different random positions. However, this invention is not limited to twelve variations and any number of charts may be designed.

In a preferred embodiment of this invention, the system further includes the key 12 for checking an observed position 22 of the shaded marks 18 in comparison to an actual position 24 of the shaded marks 18. In the embodiment shown in FIG. 2B, the key 12 comprises layout corresponding to the table layout of the chart 10 shown in FIG. 2A. The key is preferably made of a generally translucent or transparent material and includes a plurality of indicators 26 identifying locations of the plurality of shaded marks 18 on the table 10. The generally translucent or transparent material allows the key 12 to be placed on top of the chart to locate the actual positions 24 of the shaded marks 18.

Figure 3A:
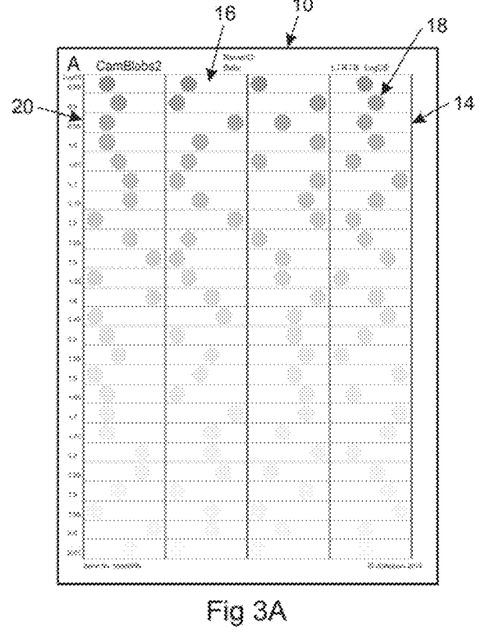
FIG. 3A-D is a sample test using the system of FIGS. 2A and 2B.
Figure 3B:
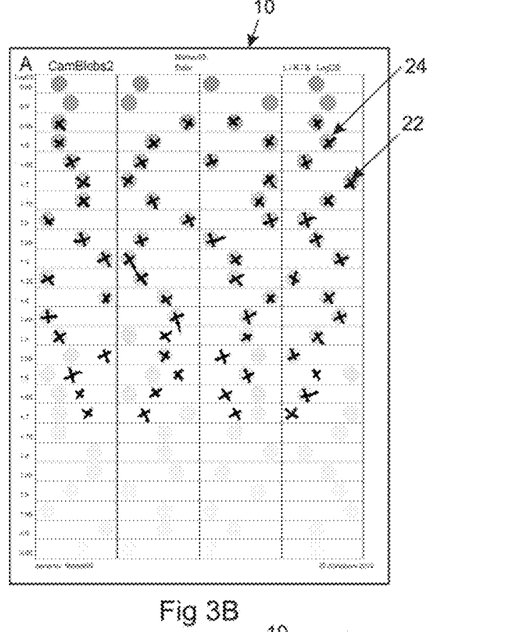
Figure 3C:
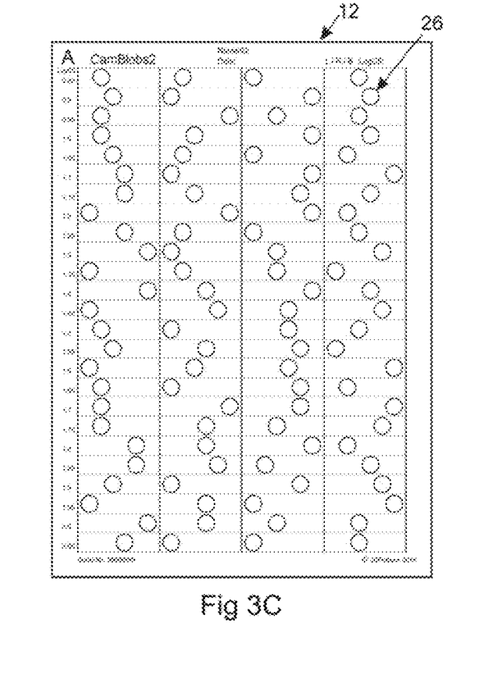
Figure 3D:
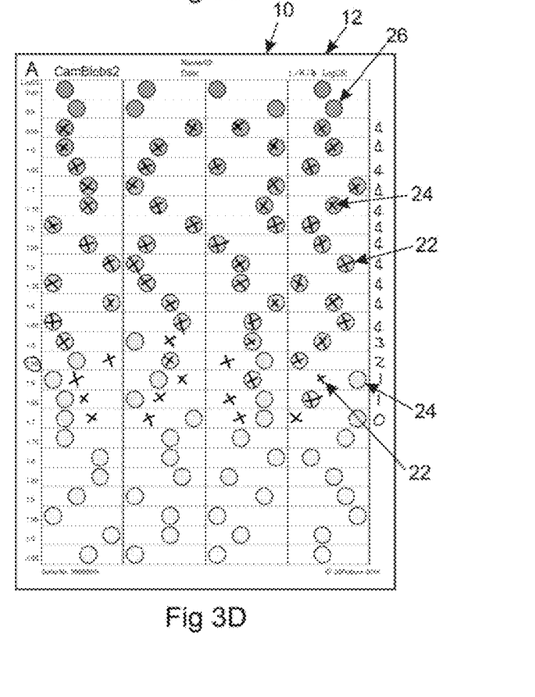

FIG. 3A-D shows an example of the steps for testing a patient's contrast sensitivity according to an embodiment of this invention. A new, blank table 10 is provided to the patient in FIG. 3A. The patient, using a reading spectacle correction if appropriate, holds the table 10 on a suitable board at a convenient distance in a light that would be good for reading, generally greater than 300 lux. Then, as shown in FIG. 3B, starting at any level of the table 10 at which the shaded marks 18 can be seen clearly, in this case the row labeled 0.95, the patient marks an observed location 22 (or a believed location) of the shaded marks 18, progressing down the table 10 until it is necessary to guess the position of the shaded marks 18 even when the table 10 has been viewed for several seconds. The patent is permitted to move the table 10 or adjust its position or distance to make the fainter shaded marks 18 easier to see. When the patient has finished marking the table 10 it is scored using a transparent overlay key 12, shown in FIG. 3C, with positions of the shaded marks 18 indicated by open circles indicators 26. In FIG. 3D, a number of correctly identified locations of each row is written in the right-hand margin of the table 10. In one embodiment, a threshold contrast sensitivity is reported as the contrast 20 of the highest row on which the patient has failed to identify the correct positions of two or more of the shaded marks 18. The threshold contrast may also be defined as the contrast of the highest line on which the subject has correctly identified the positions of no more than two of the spots (i.e. has made two or more errors). In the embodiment shown in FIG. 3D, the threshold contrast was determined to be 1.55. This test is particularly useful in assessing diabetic patients, as diabetic patients generally have lower contrast sensitivity that non-diabetic subjects. For example, it has been shown that while 95% of non-diabetic subjects have a log contrast sensitivity of greater than 1.80, 95% of diabetics with sight-threatening retinopathy have a log contrast sensitivity of lower than 1.85, in many cases much lower.

In an alternative embodiment of this invention, scoring of the chart may be accomplished using electronic means, such as photographing and/or scanning a completed test and a program would look for differences in the test page between marked and unmarked. In another embodiment, the chart of this invention may be provided on a computer with a processor, such as a tablet computer, with a touch sensitive pad and/or a stylus-type marking device.

Figure 4A:
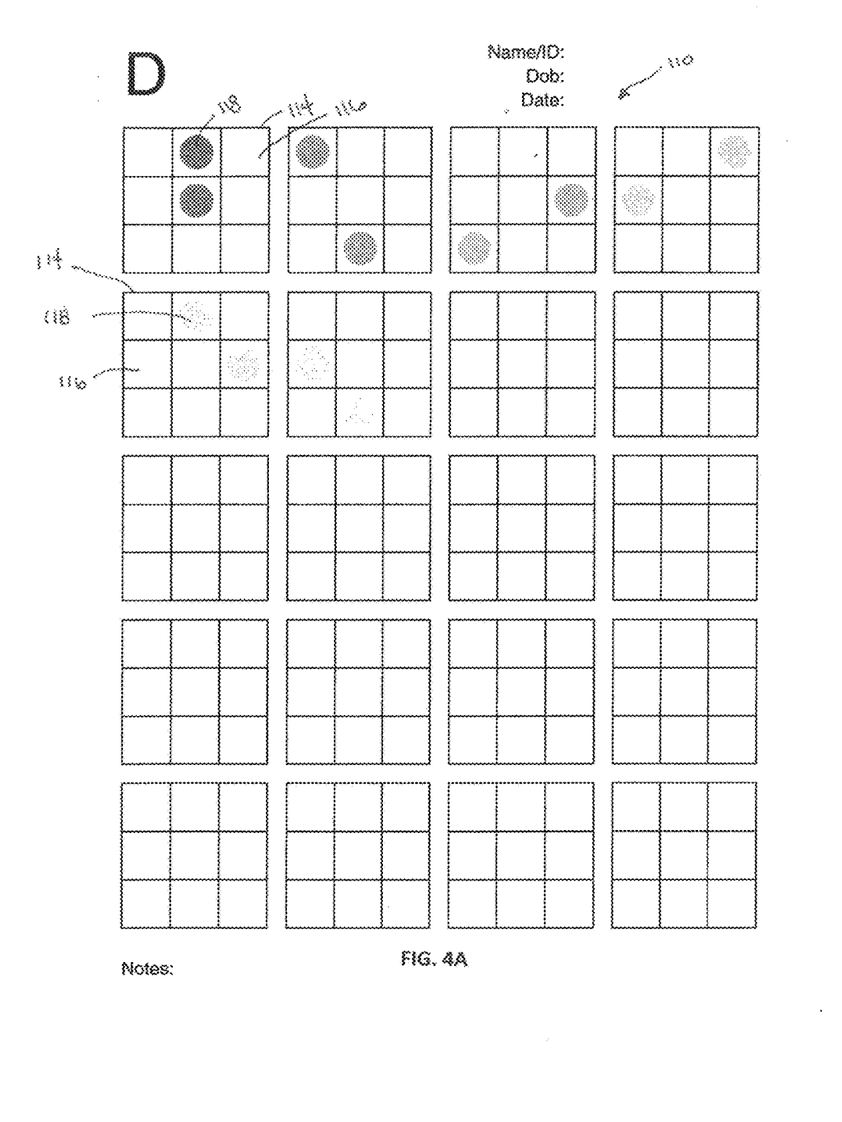
FIG. 4A is a chart for measuring contrast sensitivity according to another preferred embodiment of this invention.
Figure 4B:
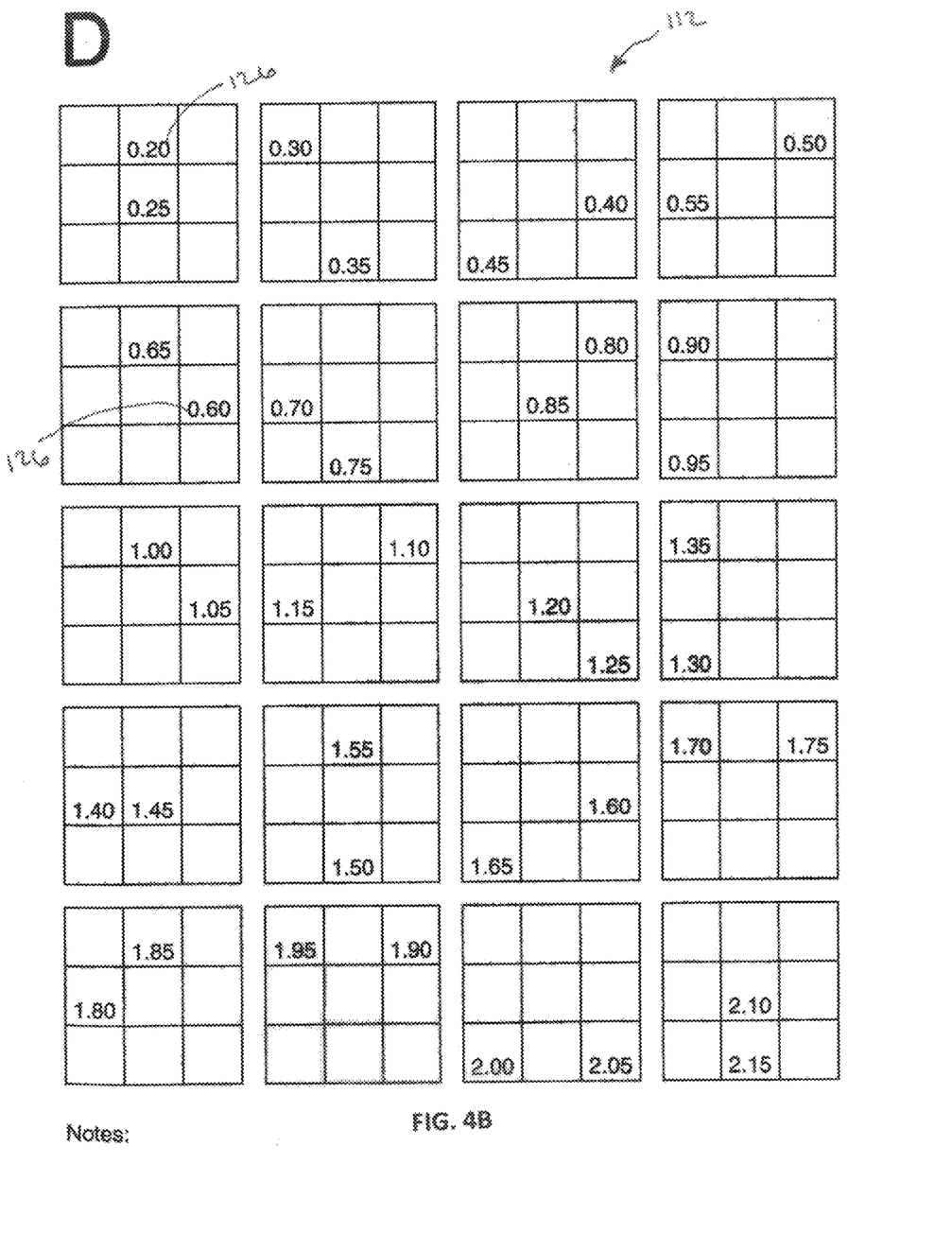
FIG. 4B is a key for the contrast sensitivity chart of FIG. 4A.

FIG. 4A illustrates a chart 110 for determining contrast sensitivity according to another embodiment of this invention. FIG. 4B illustrates a key 112 for checking the chart 110. In this embodiment, the chart 110 comprises a plurality of lattice 114 including a large square sub-divided into smaller cells 116 by thin black lines. In the embodiment of FIG. 4A, the chart 110 includes twenty lattices 114 arranged in five rows and four column. However, any arrangement of the chart 110 with a different number of rows and columns or another arrangement may be used. Each lattice 114 is sub-divided into nine cells 116 in a 3×3 arrangement. In this embodiment, the cells 116 comprise a square shape. Alternatively, the lattice may be divided into another arrangement such as a 2×2 arrangement, a 4×4 arrangement, a 3×5 arrangement, or any n×m arrangement, where n and m are integers that may or may not equal each other.

The chart 110 further includes a plurality of shaded marks 118 positioned in some of the squares 116. In the embodiment shown in FIG. 4A, each lattice 114 includes two of the nine squares randomly filled with one of the shaded marks 118. Alternative embodiments may use other ratios of shaded marks relative to squares. In this embodiment, the shaded marks 118 comprise a shaded circular spot having a 9 mm diameter. In alternative embodiment, the shaded marks 118 may not comprise a circular spot with a 9 mm diameter and may comprise any shape and/or any dimensions. However, in a preferred embodiment, the plurality of shaded marks 118 comprise a consistent shape throughout the chart 110.

As described earlier in this application, each of the shaded marks 118 include a contrast that varies across the chart 110. In this embodiment, the log of Weber contrast ranges from −0.20 to −2.15 across the chart 110. However, it should be understood that other ranges of contrast may be used. In the embodiment shown in FIG. 4A, the shaded marks 118 include a progressively decreasing contrast. In the upper left corner of the chart 110, the lattice 114 includes two shaded marks 118, one with a log Weber contrast of −0.20 and a second with a log Weber contrast of −0.25. The contrast moving from left to right and down become progressively lighter and lighter, by 0.05 log units lower, relative to the background until reaching the lower right corner with the lattice 114 including two shaded marks 118, one with a log Weber contrast of −2.10 and a second with a log Weber contrast of −2.15. However, it should be understood that other ranges of contrast and variation may be used. For example, darker contrast ratios may be used to measure contrast sensitivity in patients with more severely impaired vision.

In a preferred embodiment of this invention, the system further includes the key 112 for checking an observed position of the shaded marks 18 in comparison to an actual position of the shaded marks 18. In the embodiment shown in FIG. 4B, the key 112 comprises a layout corresponding to the layout of the chart 110 shown in FIG. 4A. The key is preferably made of a generally translucent or transparent material and includes a plurality of indicators 126 identifying locations of the plurality of shaded marks 118 on the chart 110. In this embodiment, the indicators 126 comprise an absolute value of the Weber contrast for the shaded mark 118 located in the square 116.

Similar to the description above, the patient views the chart 110 and marks an observed location by marking the squares 116 of each lattice 114 that include one of the shaded marks 118, progressing down the chart 110 until it is necessary to guess the position of the shaded marks 118 even when the chart 10 has been viewed for several seconds. When the patient has finished marking the chart 110 it is scored using the transparent overlay key 112 with positions of the shaded marks 118 indicated by Weber contrast values as the indicators 126. In an embodiment of this invention, a threshold contrast sensitivity is determined by locating the lattice with the faintest shaded marks in which both shaded marks 118 were correctly identified. However, alternative means of determining threshold contrast sensitivity may be used.

In a preferred embodiment of this invention, the charts 10, 110 of this invention and the images appearing on the charts are generated using a program written in PostScript. A standard raster-image processor, such as Colorburst Overdrive RIP, is used to interpret the PostScript program and drive a printer. The charts 10, 110 are preferably printed on one side of a matte-surfaced heavy white paper, 160 or 200 gsm, using ink-jet printers filled with pigment-based black and two lighter "black" inks, such as Piezography® neutral black series. Calibration of the printing process has been achieved by measuring the contrast of the digital images of sets of special test patterns obtained with a 1.3 Megapixel machine-vision CMOS (complementary metal-oxide semiconductor) camera using an application written in ImageJ. The printing process is preferably calibrated just prior to a print run of the charts 10, 110 and checked again after completion of the print run. Using this process, all contrast values of the shaded marks 18, 118 on the printed charts have normally been found to be within 0.01 log units of their nominal values. Any charts 10, 110 with any contrast value in error by as much as 0.02 log units are preferably discarded.

The charts 10, 110 of this invention differ from conventional printed contrast sensitivity charts in four main ways: 1) the shaded marks 18, 118 that patients are required to detect are all uniform round spots of the same size; 2) patients are required to show that they have seen the shaded marks 18, 118 by correctly reporting the position of the shaded mark rather than by identifying its shape; 3) at each contrast level, the patient is required to detect several of the shaded marks 18, 118 and 4) the patients record the location of the shaded marks by marking the chart. As such, the charts can only be used once and a new, pristine chart must be used for each test.

While previously known contrast sensitivity charts have used letters, grating patches or edges as targets, applicants of the claimed invention only know of one previous contrast test using round spots as targets, George Young Threshold Test. One version of the Young test was a little printed book with pages that were completely blank except for a single round spot about 14 mm in diameter. The spot on the first page was of a faint grey, such that a subject with normal vision could only barely see it while the spots on the succeeding seven pages were successively darker and darker grey until the last was black. Subjects were asked whether or not they could see the spot on the first page and if they said they could not they were shown the page with the next darker spot. The palest of the spots that could be seen was taken as indicating the subjects' contrast sensitivity. The Young test also included additional pages of a similar format but with other colors.

This invention preferably utilizes round shaded marks 18, 118. Round marks are preferred because round spots have the advantage that their visibility is, for a large range of sizes, essentially independent of their angular subtense at the eye. This was well established for round spots in a monumental study by Blackwell (1946) who demonstrated that the contrast threshold of normal young adults for detecting round spots at photopic levels of luminance (greater than about 40 cd m$^{-2}$) was effectively independent of the size of the round spots so long as the diameter subtended an angle greater than about 1 degree of arc. Based on these observations the diameter of the shaded marks 18, 118 on the charts 10, 110 has been set at 9 mm, the smallest size that ensures that at the distance at which the chart is viewed the contrast threshold is always close to its asymptotic minimum. Round spots that are 9 mm in diameter subtend an angle of more than 1 degree at any distance up to 52 cm and therefore have a threshold contrast that will not be significantly dependent upon the actual distance at which the charts 10, 110 are held by the patient except in so far as the threshold contrast could be increased as a result of the chart not being in focus.

However, given the way in which the charts are to be used, it may reasonably be assumed that patients will either accommodate on the chart, guided by the narrow lines printed on it or, in the case of presbyopes, hold the chart at the distance which provides the most distinct view of the lines. In either case, it can be assumed that the shaded marks will be viewed in best focus even when they are too indistinct to themselves provide a stimulus to accommodation. Should the charts be viewed binocularly, then the lines serve to control convergence.

Although Young's published threshold test was described as a simple detection task, the fact that the spots appear in arbitrarily different positions on different pages makes it seem likely that the examiner would normally be expected to confirm that subjects had really seen a spot by getting them to indicate where the spot was located on the page. This procedure automatically converts the test into a "multiple-alternative forced choice" task, a test format that requires the subject to choose between several possible responses only one of which is correct. It is not clear that Young himself recognized the desirability of using a multiple-alternative choice format although this had been evident to Snellen (1862) when creating his acuity charts. While this requirement can certainly be met for both acuity and contrast sensitivity charts by using letters that must be identified as the targets, such targets always have the residual problem that they are not all equally identifiable as well as requiring the subject to be familiar with the alphabet being used. Letter-like optotypes such as Landolt rings have been used to obviate these problems, but simple targets, spots or edges (e.g. Verbaken and Johnston, 1986) intrinsically avoid both disadvantages.

Whether targets are to be identified by their shape, by their orientation or by their position with respect to a visible reference (stimulus features that are used in other charts), the question arises of how many alternatives there should be. The more alternatives there are, the more information is provided by each response, though the advantage of increasing the number of available alternatives may be vitiated by the increased search or decision time that is required or by the increased area of the chart that must be provided for each target. In the preferred embodiment of the chart 10, the compromise adopted is to define six equally-spaced positions within each of the horizontally-elongated rectangles 16 on the chart 10 of which one is randomly chosen to be the center of the shaded mark 18 (or target) displayed in the rectangle 16. It has been found that with six defined positions subjects can unambiguously locate and mark the center of any visible spot.

Detection of targets whose contrast (or size) is close to threshold is probabilistic. This inevitably limits the reproducibility of "threshold" determinations made with a single series of targets graded in contrast (or size). To improve the reproducibility of a threshold determination, it is necessary to have the subject make repeated observations of near-threshold stimuli. When the test system permits it, this is usually accomplished by using a staircase or other adaptive procedure but where such a procedure cannot be implemented (as with a simple printed chart), some advantage can be gained by making the decision about the threshold dependent on the subject's responses to several targets at each contrast. To the extent that the subject's observations of the several targets of a given contrast are independent, the variability of a threshold determination made using a criterion based on some combination of the subject's responses will be inversely related to their number. While increasing the number of targets of each contrast certainly does decrease the variability of repeated determinations of contrast sensitivity (as demonstrated by preliminary experiments), increasing the number of observations required necessarily increases the time to mark the chart. There is also, of course, a limit to the number of observations that the subject can be asked to make that is set by the number of rectangles that can be printed on a chart of fixed size, though this is inversely dependent upon the range of contrasts that a single chart can cover. The number of repeat observations required was set at four as a heuristic compromise taking all the relevant factors into account.

Another difference between the charts 10, 110 of the claimed invention and other contrast sensitivity test charts is that the charts 10, 110 are intended to be marked by the subject using a writing utensil. This marking serves the primary purpose of making it possible for the chart to be used without the need to have an examiner present to record the subject's responses while automatically providing a permanent record of those responses. Having a test based on charts that will only be used once overcomes many of the difficulties associated with conventional printed charts. Because the charts 10, 110 will be used for only one test, the charts require very little handling and can easily be kept clean and unmarked until they are used. For the same reason, it is unnecessary for the surface of the charts to be laminated or otherwise coated to minimize the susceptibility of the charts to exposure to light or to dirt or to damage. Not requiring a coating makes the calibration of the printing process easier and simpler to implement. In all probability, the charts 10, 110 will be used much sooner after they have been printed than conventional charts and this will itself remove residual worries about the long-term stability of the calibration.

Since the charts 10, 110 will be used only once, the charts 10, 110 can be printed on much lighter paper stock than wall charts or other types of tests that will be repeatedly handled which must be printed, or subsequently mounted, on rigid board to ensure that they stay flat. The lighter stock paper also allows the charts 10, 110 of this invention to more easily lie flat. The relatively small size of the charts 10, 110 of this invention and the fact that the charts are printed on paper rather than board makes it possible to print them on simple small ink-jet printers. All these factors taken together greatly reduce the cost of producing the charts 10, 110 as well as making it practicable to have many more than the three variants in which conventional charts are normally provided.

To make charts 10, 110 for measuring contrast sensitivity that display targets 18, 118 of many different contrasts on a white background, it is necessary to have some way of reliably producing the different contrasts. Moreover, if the contrast sensitivity of normally sighted observers is to be measured, then the method to be used must be able to produce images with defined Weber contrast of substantially less than 1%. This is not easy. The George Young Threshold Test used a differently diluted ink for each of the different targets but the printing of the Young Test was simplified by having only one target on each page. The actual contrasts that were produced were uncalibrated and effectively unknown. Although modern instruments would make it possible to perform exact calibration and in principle inks could be formulated to provide the correct contrasts, printing the charts 10, 110 with 25 differently formulated inks, as required for this invention, would not be a practicable method for producing affordable charts. As an alternative to using multiple inks, one for each contrast, it is in theory possible to use a single black ink in conjunction with a half-tone printing process. In half-tone printing, the average reflectance of the printed area is reduced to the desired level by applying ink to only some fraction of the area, traditionally as an array of dots. To change this fraction, and hence to change the average reflectance of the printed image and its effective contrast when illuminated, the dots are either changed in size while keeping their separation constant or by changing the separation between the dots while keeping their size constant. However, whichever method is used, half-tone printing with black ink is only an acceptable way to produce low contrast images if the separation and size of the dots is such as to render the individual dots invisible as a result of the eye being unable to resolve them. This places a strict limit on the use of this approach that is determined by the smallest size of the dots that can be reliably printed. In practice this means that while half-tone printing with black ink can be used for charts that are to be viewed at a distance of one meter or more, it is not an acceptable way to print charts for use at reading distance.

A preferred way of printing the charts 10, 110 of this invention, with monochrome targets whose Weber contrast can be as low as 0.7%, is to use half-tone images in combination with several inks having different dilutions. This is common practice in the production of high quality black and white photographic prints and neutral "black" inks in many shades of gray are available. The charts 10, 110 of this invention are preferably printed with black ink and two lighter shades of gray ink. The charts 10, 110 are preferably printed using "stochastic screening" techniques that have irregularly spaced dots to minimize the visibility of the regular arrays of dots used in conventional printing.

For any chart to provide a correct estimate of a subject's contrast sensitivity it is obviously necessary for the luminance contrast of the different targets to be sufficiently close to their nominal values in the situation in which the chart is being viewed. To make sure that the contrast values are correct is not an entirely trivial matter. In the case of printed charts we can distinguish three kinds of problem: a) charts can become faded, dirty or marked, b) the contrast of the targets can differ from the nominal value because the illumination under which the chart is being viewed differs from that under which the printing process was calibrated and c) charts can be wrongly printed or the printing process wrongly calibrated.

a) The effects of dirt and damage as well as fading of the ink and changes in reflectance of the paper substrate are effectively obviated by the careful storage of unused disposable charts in the dark.

b) To the extent that the reflectance of the printed areas of the chart does not depend upon wavelength in exactly the same way as that of the unprinted substrate, the luminance contrast of the targets will potentially be dependent upon the spectral composition of the illuminating light. While this would be of no consequence if the spectral composition of the light illuminating the chart when it is being used to measure contrast sensitivity is the same as that used to calibrate the printing process, this will not necessarily be the case. Even if the apparent color of the light illuminating the chart is the same (white) as that of the calibrating light this does not guarantee that the luminance contrast of the targets will exactly correspond to the nominal value established by the calibration process because the apparent color of a light does not determine the exact form of its spectral distribution. As an example, light from "white" light-emitting diodes (LEDs) may be indistinguishable from the light produced by an incandescent source even though the spectrum of the LED light will normally be relatively deficient in the cyan region of the spectrum (around 500 nm). The contrast difference related to this spectral difference will be greatest in the case of the lightest grey ink that is used but with appropriate choice of ink this effect can be minimized and for the charts 10, 110 of this invention is less than 0.02 log units at all levels for lights that are visibly white. Again, if the printed and unprinted areas of the chart 10, 110 have different specular reflectance then there will generally be a change in the luminance contrast with changes in the angle of incidence of the illuminating light as well as with changes in the viewing angle. This effect, as well as the effect introduced by spectral differences between the illumination used for testing and calibration, is minimized by choosing both the paper and the ink to have matte surfaces with the lowest possible levels of specular reflectance. Even so, it is desirable that the illumination of the chart when it is in use should be arranged so as to reduce the contribution of specular reflections as far as possible. This means that the source of light should be diffuse, or, if the light is from focal sources, these should not be too close to the line of sight. Another potential problem relates to the possibility of there being a significant amount of ultraviolet (UV) radiation in the chart illumination, as will be the case with sunlight and may be with light from fluorescent and even incandescent lamps. This can affect the visual contrast of a printed chart if the substrate on which the chart is printed contains "optical brightening agents (OBAs)", fluorescent compounds that convert UV into visible blue light. As such, the charts 10, 110 of this invention are preferably printed on paper that does not contain OBAs.

c) The contrast that is achieved by printing a target depends upon a number of factors, but the only one that can be adjusted at the time a chart is being printed is the tonal value of the target areas (the tonal value can be thought of as the proportion of the area that has been inked). The required value must be ascertained by reference to measurements of the contrast achieved in preliminary prints of appropriate targets with a range of different tonal values. Having fitted a suitable mathematical function relating achieved contrast to tonal value, the tonal values to be used for the targets to be printed on the contrast sensitivity charts can readily be calculated. It is difficult to check directly that the contrast of the small targets on printed charts 10, 110, as such it is normally necessary to rely on the preliminary calibration of the printing process to ensure that the contrast is correct. However, it must be recognized that the ink-jet printing process is somewhat sensitive to environmental and other factors that cannot be completely controlled and that there may be slow changes in the precise relation between achieved contrast and the set tonal value. For this reason, a calibration procedure must be repeated at regular intervals during printing to make sure that there has been no significant change or, if there has been, to take appropriate action in rejecting charts which may possibly have the wrong contrast as well as to calculate revised tonal value settings.

Figure 5:
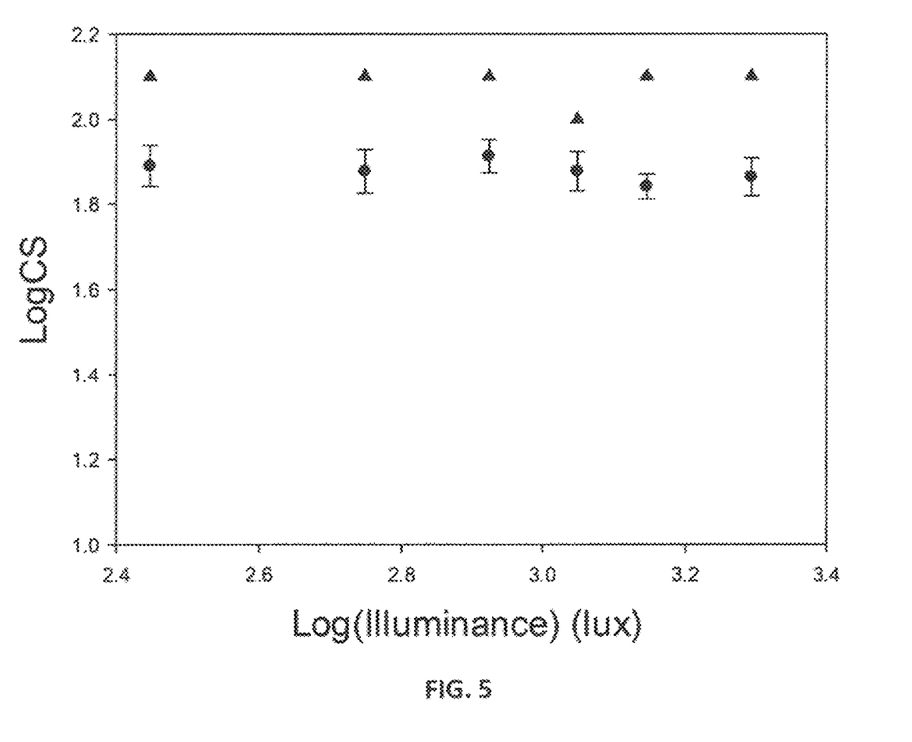
FIG. 5 shows result of a test measuring binocular contrast sensitivity.

As noted earlier, the contrast sensitivity charts 10, 110 of this invention were designed to be used without a professional examiner and in less well controlled circumstances than would be found in a clinic. It is also expected that the charts 10, 110 will be used without any facility to measure the exact light level and without precise control of the distance of the chart 10, 110 from the subject. Thus, measurements made with the charts 10, 110 must be essentially unaffected by the level of illumination and by the distance of the charts from the subject's eyes. While reference to previous studies suggested that these requirements would be adequately met by the design that has been described, it was felt to be desirable to examine just how nearly they had been met. In testing, measurements of binocular contrast sensitivity were made using multiple versions of the charts 10, 110 of this invention with illumination levels between 280 and 1960 lux provided by 1 to 7 white LED bulbs placed 90 cm away from the charts 10, 110. These light levels correspond to what are typically described as being suitable for all kinds of office work, from the easiest to the most exacting. FIG. 5 shows the result of such measurement series. The effect on measured contrast sensitivity of changing the illumination over this seven-fold range was in all cases less than 0.05 log units, i.e. less than one of the steps of contrast between target rows on the chart.

Figure 6:
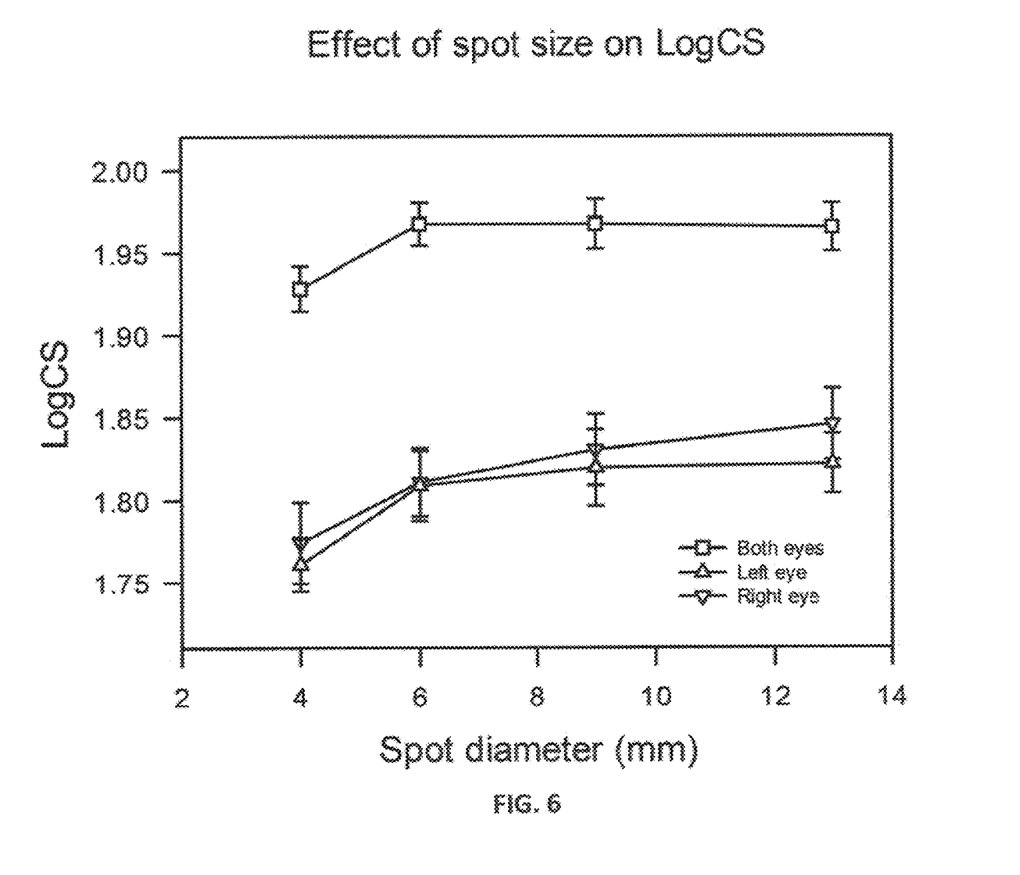
FIG. 6 shows results of a test measuring both monocular and binocular contrast sensitivity of normal adult subjects.

Changing the viewing distance of the chart changes the angular subtense of the target spots at the subject's eye and can potentially affect their focus. Since, as previously noted, it can be assumed that the subject will hold the chart at whatever distance brings the lines on the chart 10, 110 into best focus, the primary question is whether the contrast threshold for the target spots 18, 118 depends upon their angular subtense when this varies over the range set by the requirement that the chart is to be held and marked by the subject. This has been examined by measuring contrast sensitivity with specially printed charts 10, 110 having spots with diameters 4, 6, 9 and 13 mm. When 6 and 13 mm spots are viewed at the normal reading distance of 40 cm they will subtend the same angle as the standard 9 mm spots when the chart is held either as far away or as near as possible. The result of single measurements of both the monocular and binocular contrast sensitivity of normal adult subjects is shown in FIG. 6. It can be seen that over the range of spot size from 6 to 13 mm (corresponding to the available range of angular subtense of the standard spots 18, 118) there is very little difference in the measured contrast sensitivity, certainly very much less than the preferred contrast step size (0.05 log units) of the charts 10, 110. It is interesting to note that for all spot sizes the binocular contrast sensitivity is very close to 0.15 log units greater than the monocular sensitivity. This is in agreement with the value found in other studies for the relation between monocular and binocular contrast sensitivity when there is no difference in sensitivity between the eyes.

Thus the invention provides a chart and method for measuring contrast sensitivity in a variety of lighting situations and from a range of viewing distances.

While in the foregoing specification this invention has been described in relation to certain preferred embodiments thereof, and many details have been set forth for purpose of illustration, it will be apparent to those skilled in the art that the device and placard are susceptible to additional embodiments and that certain of the details described herein can be varied considerably without departing from the basic principles of the invention.

The invention claimed is:

1. An apparatus for measuring contrast sensitivity, the apparatus comprising:
   a table arranged in rows and columns of cells, the cells having a white background; and
   a plurality of shaded marks, each shaded mark of the plurality of shaded marks including a predetermined contrast relative to the background wherein one of the plurality of shaded marks is randomly positioned in a particular horizontal alignment within one or more of the cells.

2. The apparatus of claim 1 further including:
   a key comprising a generally translucent or transparent material with a plurality of indicators identifying locations of the plurality of shaded marks, wherein the key is overlaid on top of the chart.

3. The apparatus of claim 1, wherein the table includes twenty-five rows and four columns of cells, wherein the cells comprise elongated rectangles.

4. The apparatus of claim 3, wherein each of the plurality of elongated rectangles includes the shaded mark positioned in one of six positions within the elongated rectangle.

5. The apparatus of claim 1, wherein the shaded mark comprises a circular spot.

6. The apparatus of claim 5, wherein the circular spot comprises a diameter of 9 mm.

7. The apparatus of claim 1, wherein the contrast of each of the shaded marks comprise a log of Weber contrast ranging from −0.85 to −2.05 as an integral multiple of 0.05.

8. The apparatus of claim 7, wherein the plurality of shaded marks in each of the rows comprise the same Weber contrast.

9. The apparatus of claim 7, wherein the plurality of shaded marks become progressively lighter moving down the columns.

10. A method of using the apparatus of claim 1 comprising:
    marking an observed position of the shaded mark in each of the plurality of cells; and
    overlaying a key on the apparatus to check the observed position; and
    checking the observed position against an actual position of the shaded mark to determine a threshold contrast.

11. The method of claim 10, wherein the threshold contrast is defined as the highest row on which two or fewer of the marked positions match the actual positions.

12. An apparatus for measuring contrast sensitivity, the apparatus comprising:
    a chart including a plurality of lattices, each of the lattices including a plurality of cells;
    a plurality of shaded marks, wherein a minority of the cells in each of the lattices include one of the plurality of shaded marks, wherein a contrast of each of the plurality shaded marks varies; and
    a key comprising a generally translucent or transparent material with a plurality of indicators identifying locations of the plurality of shaded marks, wherein the key is overlaid on top of the chart.

13. The apparatus of claim 12, wherein each of the plurality of lattices includes nine cells and two of the nine cells includes one of the plurality of the shaded marks.

14. The apparatus of claim 12, wherein each of the plurality of the shaded marks comprise a circular spot.

15. The apparatus of claim 14, wherein the circular spot comprises a diameter of 9 mm.

16. The apparatus of claim 14, wherein the plurality of shaded marks comprise a log of Weber contrast ranging from −0.20 to −2.15 as integral multiples of 0.05.

17. The apparatus of claim 16, wherein the key indicates the log of Weber contrast for each of the plurality of shaded marks.

18. The apparatus of claim 17, wherein the plurality of shaded marks become progressively lighter moving from left to right and down from an upper left lattice to a lower right lattice.

19. A method of using the apparatus of claim 12 comprising:
    signaling an observed position of one or more of the shaded marks positioned in each of the plurality of lattice;
    overlaying the key on the apparatus; and checking the observed position against an actual position of the one or more shaded marks to determine a threshold contrast.

20. The method of claim 19, wherein the threshold contrast is defined as the highest log of Weber contrast in which neither of the recorded positions of the lattice match the actual position.

\* \* \* \* \*